(12) United States Patent
Snyder et al.

(10) Patent No.: US 8,679,314 B1
(45) Date of Patent: Mar. 25, 2014

(54) METHANE PRODUCTION USING RESIN-WAFER ELECTRODEIONIZATION

(71) Applicants: Seth W. Snyder, Lincolnwood, IL (US); YuPo Lin, Naperville, IL (US); Meltem Urgun-Demirtas, Naperville, IL (US)

(72) Inventors: Seth W. Snyder, Lincolnwood, IL (US); YuPo Lin, Naperville, IL (US); Meltem Urgun-Demirtas, Naperville, IL (US)

(73) Assignee: U.S. Department of Energy, Washington, DC (US)

( * ) Notice: Subject to any disclaimer, the term of this patent is extended or adjusted under 35 U.S.C. 154(b) by 58 days.

(21) Appl. No.: 13/648,319

(22) Filed: Oct. 10, 2012

(51) Int. Cl.
*B01D 61/48* (2006.01)
*C02F 11/04* (2006.01)

(52) U.S. Cl.
USPC ........... 204/524; 204/530; 204/533; 204/536; 204/632

(58) Field of Classification Search
USPC .......................... 204/632, 524, 530, 533, 536
See application file for complete search history.

(56) References Cited

U.S. PATENT DOCUMENTS 8,580,096 B2 * 11/2013 St. Martin et al. ............ 204/524

* cited by examiner

*Primary Examiner* — Arun S Phasge
(74) *Attorney, Agent, or Firm* — John D. Cravero; Brian J. Lally; John T. Lucas

(57) ABSTRACT

The present invention provides an efficient method for creating natural gas including the anaerobic digestion of biomass to form biogas, and the electrodeionization of biogas to form natural gas and carbon dioxide using a resin-wafer deionization (RW-EDI) system. The method may be further modified to include a wastewater treatment system and can include a chemical conditioning/dewatering system after the anaerobic digestion system. The RW-EDI system, which includes a cathode and an anode, can either comprise at least one pair of wafers, each a basic and acidic wafer, or at least one wafer comprising of a basic portion and an acidic portion. A final embodiment of the RW-EDI system can include only one basic wafer for creating natural gas.

25 Claims, 6 Drawing Sheets

METHANE PRODUCTION USING RESIN-WAFER ELECTRODEIONIZATION

GOVERNMENT INTERESTS

The United States Government has rights in this invention pursuant to Contract No. DE-AC02-06CH11357, between the U.S. Department of Energy (DOE) and UChicago Argonne LLC, representing Argonne National Laboratory.

FIELD OF THE INVENTION

One or more embodiments of the present invention relate to the production of natural gas. More particularly, the invention relates to systems and methods for producing a methane-enriched natural gas stream using an anaerobic digester and resin-wafer electrodeionization (RW-EDI) system.

BACKGROUND

Natural gas (methane) has developed into a fungible form of clean energy, and its adoption is increasing. Methane is the desired result of carbon dioxide being separated from biogas. Anaerobic digestion, which is a process that breaks down biomass and other carbonaceous feedstocks, is utilized to create biogas. Although biogas is created as a result of anaerobic digestion, the process to produce a fungible natural gas is not complete because carbon dioxide must be separated from the biogas to create the desired high methane concentration in fungible natural gas. Current methods to separate carbon dioxide include utilizing a vacuum to pull carbon dioxide across a membrane or from a solvent and elevating the temperature of a solvent to drive the carbon dioxide. However, this imparts high energy costs. An ideal method of isolating carbon dioxide would be cost efficient and would have low capture energy consumption.

SUMMARY

One or more embodiments of the invention is directed to a method for the production of methane-enriched natural gas in an integrated biodigestion and resin-wafer electrodeionization (RW-EDI) system including the steps of: (1) anaerobically digesting a biomass or other carbonaceous feedstock to produce a biogas stream, a supernatant stream and a biodigestate stream, and (2) introducing the biogas stream and the supernatant stream to a RW-EDI system to produce methane, $CO_2$ and a bicarbonate-depleted stream of fluid. Biomass and other carbonaceous feedstock include, but are not limited to: sludge from wastewater treatment plants, animal manure, plant residues, agricultural residues, algal biomass, municipal solid waste, wood and paper residues, coal, pet coke and hydrocarbon residues, organic solid waste, lignocellulosic materials, forest residue, and food wastes. Throughout this document, the term biomass refers to all of these feedstocks. The methane and $CO_2$ are removed from the RW-EDI system and collected separately for further use or processing and the bicarbonate-depleted stream is removed and recirculated to the system. Alternatively, or additionally, a bicarbonate stream can be produced and removed from the RW-EDI system and reintroduced to the system. In additional embodiments, the method can optionally include steps of treating a wastewater stream to obtain a biomass and further adding a thickener to increase solid content of the biomass.

One or more embodiments of the present invention also relate to a system for generating a renewable natural gas comprising an anaerobic digestion apparatus and RW-EDI apparatus in fluid communication with each other. The anaerobic digestion apparatus includes a biomass inlet, a biogas outlet, a supernatant outlet, and a biodigestate outlet. The system also includes a RW-EDI apparatus composed of a biogas inlet, a supernatant inlet, a natural gas outlet, a bicarbonate outlet, a carbon dioxide outlet, and a bicarbonate depleted stream outlet. In one or more embodiments, the biogas outlet and the supernatant outlet of the anaerobic digestion apparatus are in fluid communication with the RW-EDI system. In an additional embodiment, the system further comprises a wastewater treatment apparatus composed of a wastewater inlet, a treated water outlet, and a biomass outlet.

In one embodiment of the system, the RW-EDI apparatus comprises a cathode and an anode that are separated by one or more pairs of porous solid ion exchange resin wafers arranged in stack. Each pair comprises a basic wafer and an acidic wafer, with a cation ion exchange membrane between the basic wafer and the acidic wafer in each pair. The cathode and a basic wafer are separated by a bipolar ion exchange membrane, and the anode and an acidic wafer are separated by a bipolar membrane. Each pair of wafers is separated from any adjacent pair by a bipolar ion exchange medium. Each basic wafer comprises a porous basic ion exchange medium, and each acidic wafer comprises a porous acidic ion exchange medium. In this embodiment, each basic wafer comprises a biogas inlet, a supernatant inlet, a methane outlet, and a bicarbonate outlet. In each acidic wafer, there is a bicarbonate inlet, a carbon-dioxide outlet, and a bicarbonate-depleted stream outlet.

In an additional embodiment of the system, minerals rich in alkaline silicates are added to the anaerobic digestion apparatus to convert $CO_2$ to carbonates and sequester them as insoluble alkaline carbonates as depicted in U.S. Pat. No. 8,247,009, which is incorporated by reference herein. The anaerobic digestion apparatus partially depleted of $CO_2$, is in fluid communication with the RW-EDI apparatus.

Advantages of the process and system described herein include a cost-effective way to produce highly concentrated natural gas with little to no $CO_2$ present. In addition, the process is an energy-efficient alternative to current methods of producing methane and separating $CO_2$. Moreover, the phosphate-rich supernatant and centrate streams produced as a result of anaerobic digestion and physiochemical conditioning, respectively, can be used as an extractant in the RW-EDI system to remove the $CO_2$ contained within the biogas. The multiple embodiments presented herein can also improve the anaerobic digester performance and accelerate biogas production by recycling bicarbonates from the RW-EDI apparatus back to the digester, thereby maintaining stable pH and alkalinity in the digester. Finally, the multiple embodiments reduce greenhouse gas emissions during the anaerobic digestion of organic materials as the carbon dioxide is converted to bicarbonates.

BRIEF DESCRIPTION OF THE DRAWINGS

These and other features, aspects, and advantages of the multiple embodiments of the present invention will become better understood with reference to the following description, appended claims, and accompanied drawings where:

DETAILED DESCRIPTION

Figure 1:
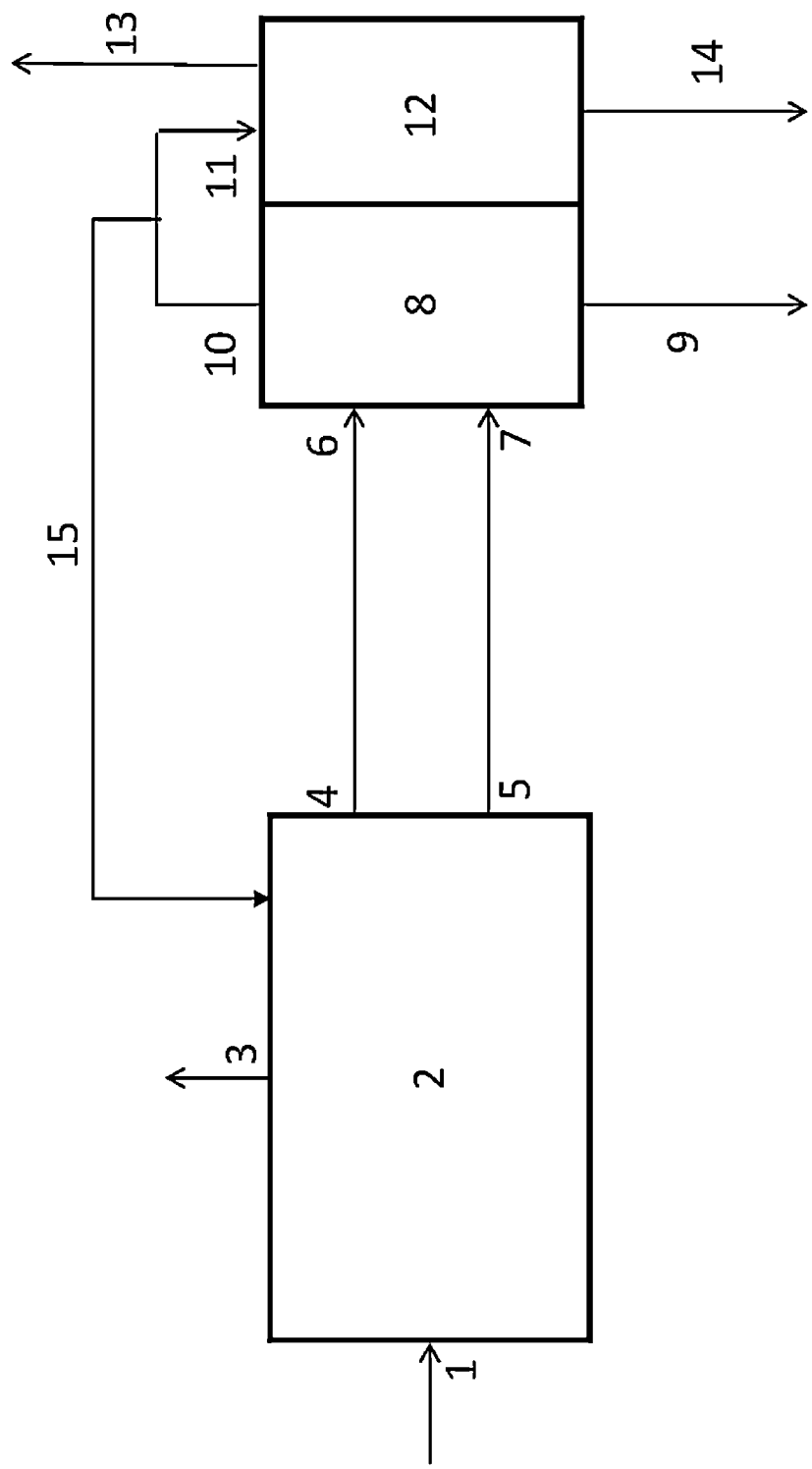
FIG. 1 represents one embodiment of the system of producing methane-enriched natural gas using an anaerobic digester and RW-EDI apparatus.

One embodiment of the present invention provides a method for the production of a renewable natural gas or methane-enriched natural gas in an integrated biodigestion and resin-wafer deionization (RW-EDI) system. The method comprises: (1) anaerobically digesting a biomass to produce a biogas stream, a supernatant stream, and a biodigestate stream; and, (2) introducing the biogas stream and supernatant stream to a RW-EDI system to independently produce methane-enriched natural gas and $CO_2$. Subsequently, the $CO_2$ and natural gas are removed from the RW-EDI system for collection.

In the initial step of anaerobic digestion, biomass is broken down to create biogas, a supernatant, and a biodigestate. Biomass includes, but is not limited to. Biogas is typically composed of methane, $CO_2$ and other gases. Biodigestate includes, but is not limited to, remnants of original biomass material that was not broken down as well as materials generated during anaerobic biodigestion. Its applications include low-grade building products and fertilizer, but it can also be sent for further processing.

Exemplary anaerobic digestion systems include but are not limited to batch or continuous systems and single-stage and two-stage digestion systems utilizing mesophilic and/or thermophilic digestion. The anaerobic digestion system may include alkaline silicate minerals that at least partially sequester $CO_2$ as insoluble alkaline carbonates, as described in U.S. Pat. No. 8,247,009. While any anaerobic digestion system can be used with the multiple embodiments described herein, a preferred embodiment includes an acid phase digester and a gas phase digester. The acid phase digester converts organic matter into soluble compounds and fatty acids. It comprises liquefaction, or hydrolysis, where the biomass is dissolved, and acidogenesis in which the dissolved solids are converted into organic acids by acidogenic bacteria. Next, the gas phase converts the soluble matter into the desired biogas through acetogenesis and methanogenesis. In acetogenesis, the organic acids are converted into acetate by acetogens. Similarly, in methanogenesis, methanogen use the products of acetogenesis and covert them to the biogas, supernatant, and biodigestate.

In one or more embodiments, the process may further comprise the steps of treating a wastewater to produce a biomass stream and thickening the biomass. In this embodiment, an initial wastewater stream is introduced into a wastewater treatment process. The initial wastewater includes, but is not limited to, a stream of water containing waste matter, including but not limited to solid waste, discarded organic plant matter, and food waste. The treatment process treats the wastewater stream producing a treated wastewater stream and biomass as a result. The treated wastewater is wastewater that contains negligible to no amount of waste matter. Biomass includes, but is not limited to, waste matter isolated from the treated wastewater.

The treated wastewater is then removed from the system, while the biomass may be conveyed to a process to thicken the biomass. The thickened biomass has a 2-10% solid concentration due to the addition of a thickener. Exemplary embodiments of thickeners may include gravity thickeners, dissolved air flotation thickeners, rotary drum thickeners, and centrifuge thickeners. The thickeners usually run with the chemicals, such as polymers, to increase the solid concentration further.

The biomass is then transported to an anaerobic biodigester, where it breaks down the thickened biomass and produces a biogas, a supernatant and a biodigestate. The biogas stream contains a combination of methane, $CO_2$ and other gases, which are transported to the RW-EDI system. The supernatant stream contains elevated levels of biochemical oxygen demand (BOD) and chemical oxygen demand (COD) and has a range of 1,000-11,500 mg/L suspended solids. The typical value of suspended solids is 4,500 mg/L.

The biodigestate may optionally be further treated through chemical conditioning. In such an embodiment, the biodigestate is moved to a chemical conditioning/dewatering apparatus and undergoes further treatment to create a centrate stream and a refuse stream. Any chemical conditioning and dewatering methods known to one of skill in the art are compatible with the one or more embodiments described herein. The refuse stream includes, but is not limited to, material isolated from the treated biodigestate stream. The refuse stream can either be disposed of or sent away for further treatment and/or use. The centrate stream may combine with the supernatant stream before entering the RW-EDI system. The centrate stream can either be a thickening centrate or a dewatering centrate. A thickening centrate has a BOD range of 170-3,000 mg/L, with a typical value of 1,000 mg/L. It is also composed of suspended solids, with a range of 500-3,000 mg/L and a typical value of 1,000 mg/L. The dewatering centrate has a ROD range of 100-2,000 mg/L, with a typical value of 1,000 mg/L. It is also composed of suspended solids, with a range of 200-20,000 mg/L and a typical value of 5,000 mg/L.

After anaerobic digestion, and optional wastewater treatment, biomass thickening and chemical conditioning, the supernatant and biogas are introduced to the RW-EDI system to produce natural gas and $CO_2$, which are subsequently removed from the system. An exemplary RW-EDI system is depicted in U.S. Pat. Publn. No. 20100300894, which is incorporated by reference herein. Generally, the RW-EDI system comprises a basic portion, an acidic portion, and anode and a cathode. A bicarbonate-depleted stream may also be produced and recycled into the initial wastewater stream before it enters the wastewater treatment process. Alternatively, bicarbonate stream from the basic compartment of the RW-EDI system may be removed, partially, from the RW-EDI system and circulated to the anaerobic digester to maintain the alkalinity of that process.

Upon introduction of the biogas and supernatant to the basic portion of the RW-EDI system, $CO_2$ in the biogas is converted to bicarbonate ion leaving a concentrated stream of natural gas. The $CO_2$-depleted, methane-enriched natural gas is collected, or otherwise removed, from the basic portion, while the bicarbonate ion flows into the acidic portion of the RW-EDI system that is in fluid communication with the basic portion. In the acidic portion, the bicarbonate is converted back to $CO_2$, which is collected or otherwise removed as a concentrated $CO_2$ stream from the acidic portion. The remaining bicarbonate-depleted stream is also removed from the acidic portion and, in alternative embodiments, may be recirculated to various portions of the system. In another embodiment, a portion of the bicarbonate ion stream may be removed from the basic portion and recirculated to the anaerobic digestions system to maintain alkalinity, instead of being transported to the acidic portion.

One or more additional embodiments relate to a system of producing methane-enriched natural gas, comprising: an anaerobic digestion apparatus comprising a biomass inlet, a biogas outlet, a supernatant outlet, and a biodigestate outlet; and a resin-wafer electrodeionization (RW-EDI) apparatus comprising a biogas inlet, a supernatant inlet, a methane outlet, and a $CO_2$ outlet. While described above as two streams, the supernatant stream (outlet and inlet) and biodigestate stream (outlet and inlet) are typically contained in the same conduit or stream, e.g., in a pipe, and such a configuration is within the scope of the multiple embodiments described herein. In other words, the terms supernatant outlet and biodigestate outlet may refer to the same outlet.

In one or more additional embodiments of the system, the system optionally includes a wastewater treatment system, a biomass thickening apparatus, a physiochemical conditioning/dewatering apparatus or a filter as described in more detail below.

FIG. 1 illustrates one embodiment of the system comprising an anaerobic digester [2] for forming biogas, and a RW-EDI system [8] and [12], for forming natural gas [7]. The anaerobic digester [2] contains a biomass inlet [1], a biogas outlet [4], a biodigestate outlet [3], and a supernatant outlet [5]. The RW-EDI system has, at least, a $CO_2$ Capture portion [8], a $CO_2$ Release portion [12], a cathode and an anode, not depicted. The $CO_2$ Capture portion, which can be a basic wafer, or alternatively a basic portion of the wafer, is used to capture $CO_2$ gas and convert it to bicarbonate, and release methane-enriched natural gas. The $CO_2$ Capture portion [8] has a biogas inlet [6], a supernatant inlet [7], a natural gas outlet [9], and a bicarbonate stream outlet [10]. The supernatant inlet [7] is in fluid communication with the supernatant outlet [5], and the biogas inlet [6] is in fluid communication with the biogas outlet [4] of the anaerobic digestion system [2]. The $CO_2$ Release portion [12], which can either be an acidic wafer, or alternatively an acidic portion of the wafer, converts the bicarbonate into pure $CO_2$, resulting in the release of $CO_2$ gas through a $CO_2$ outlet [13] and a bicarbonate-depleted stream. The $CO_2$ Release portion [12] has a bicarbonate inlet [11], a $CO_2$ outlet [13], and a bicarbonate-depleted stream outlet [14]. The bicarbonate inlet [11] is in fluid communication with the bicarbonate outlet [10]. Although not required, the system may also include a pathway [15] for a bicarbonate stream to be recirculated to the anaerobic digester [2] to maintain the alkalinity in the digester.

While described as two outlets and streams, the supernatant [5] and biodigestate [3] are typically removed from the anaerobic digester in the same conduit, e.g., pipe, and such a configuration is within the scope of the multiple embodiments described herein. In the case of a single outlet and stream of supernatant and biodigestate, a filter, not depicted in FIG. 1 but discussed below, will be utilized prior to introduction of the stream to the RW-EDI system. For example, the biodigestate and supernatant would both exit the digester together through [5] and the solids would be removed by the processes described in FIG. 3, then a filter if necessary and the remaining supernatant would enter the RW-EDI system at [7].

During use, biomass is introduced to an anaerobic digester [2] to create a biogas and supernatant which are transported to a RW-EDI system. As the biogas flows into an aqueous fluid within each wafer via gas inlet structures, an electric potential is applied across the cathode and the anode. The basic ion exchange medium converts the $CO_2$ into bicarbonate ion, and the newly formed methane-enriched natural gas is collected from each wafer through the outlet [9]. The bicarbonate-rich aqueous fluid, propelled by the gas stream, flows from the $CO_2$ Capture portion [8] into the $CO_2$ Release portion [12] via a fluid passageway. The bicarbonate-rich fluid is converted into gaseous $CO_2$ by the acidic ion exchange medium of the $CO_2$ Release portion [12]. Each $CO_2$ Release portion [12] includes a $CO_2$ outlet [13] to collect gaseous $CO_2$ out of the portion [12]. The bicarbonate-depleted stream [14] flows out of the $CO_2$ Release portion [12] and may combine with an initial wastewater stream. The flow of bicarbonate-rich fluid from the $CO_2$ Capture portion to the $CO_2$ Release portion, and subsequent conversion of the bicarbonate ion to gaseous $CO_2$ in the $CO_2$ Release portion effectively prevents any net flow of bicarbonate ions from one pair of wafers to another pair of wafers, or from one wafer to another wafer. Bipolar ion exchange membranes allow balancing counter ions to flow from one wafer to another as well as to the cathode and the anode, such that there is a net flow of protons toward the cathode and a net flow of hydroxyl ions toward the anode, thereby maintaining a basic pH in basic ion exchange medium and an acidic pH in acidic ion exchange medium.

Figure 2:
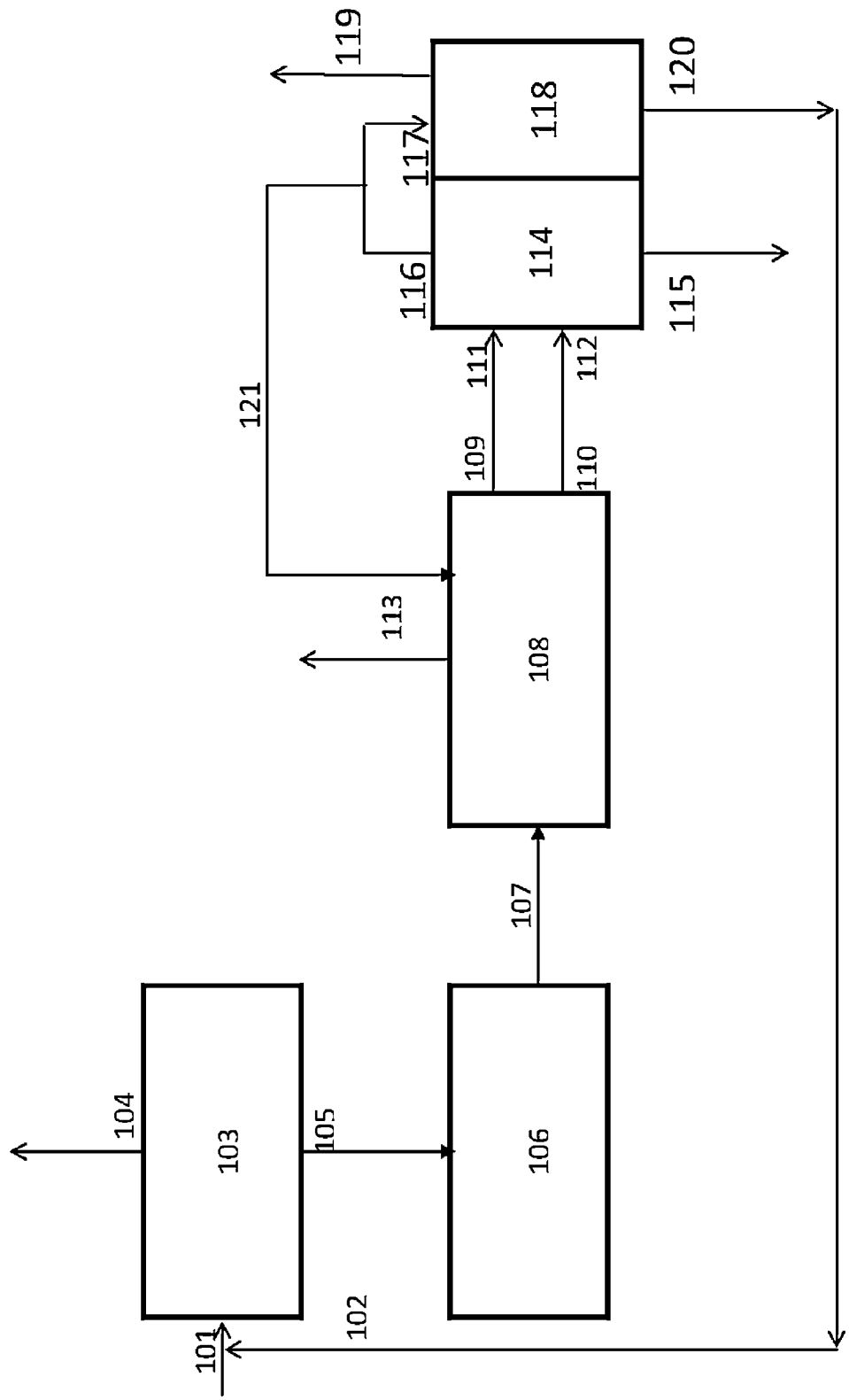
FIG. 2 represents an additional embodiment of the system for producing natural gas using a wastewater treatment system.

FIG. 2 depicts another embodiment of the system in which a wastewater treatment process is carried out before the process of anaerobic digestion to acquire the biomass. A wastewater treatment system [103] includes an initial wastewater inlet [101], which may be in fluid communication with the bicarbonate-depleted outlet [120] from the $CO_2$ Release portion [118] of the RW-EDI system. The system [103] includes a biomass outlet [105] and a treated wastewater outlet [104]. The biomass outlet [105] may be in fluid communication with the biomass thickener apparatus [106]. The thickener apparatus [106] includes a thickened biomass outlet [107] that is in fluid communication with the anaerobic digestion system [108].

The anaerobic digester [108] contains a biomass inlet [107], a biogas outlet [109], a biodigestate outlet [113], and a supernatant outlet [110]. The RW-EDI system has, at least, a $CO_2$ Capture portion [114], a $CO_2$ Release portion [118], a cathode and an anode, not depicted. The $CO_2$ Capture portion, which can be a basic wafer, or alternatively a basic portion of the wafer, is used to capture $CO_2$ gas and convert it to bicarbonate, and release $CO_2$-depleted, methane-enriched biogas. The $CO_2$ Capture portion [114] has a biogas inlet [111], a supernatant inlet [112], a $CO_2$-depleted, methane-enriched biogas outlet [115], and a bicarbonate stream outlet [116]. The supernatant inlet [112] is in fluid communication with the supernatant outlet [110], and the biogas inlet [111] is in fluid communication with the biogas outlet [109] of the anaerobic digestion system [108]. The $CO_2$ Release portion [118], which can either be an acidic wafer, or alternatively an acidic portion of the wafer, converts the bicarbonate into pure $CO_2$, resulting in the release of $CO_2$ gas through a $CO_2$ outlet [119] and a bicarbonate-depleted stream [120]. The $CO_2$ Release portion [118] has a bicarbonate inlet [117], a $CO_2$ outlet [119], and a bicarbonate-depleted stream outlet [120]. The bicarbonate inlet [117] is in fluid communication with the bicarbonate outlet [116]. Although not required, the system may also include a pathway [121] for a bicarbonate stream to be recirculated to the anaerobic digester [108] to maintain the alkalinity in the digester.

In use, the treated wastewater is removed from the system [103] through the treated wastewater outlet [104], while the biomass is conveyed into the thickening apparatus [106]. The thickened biomass is then transported to the anaerobic biodigester [108], where it breaks down the thickened biomass and produces a biogas, a supernatant and a biodigestate.

Figure 3:
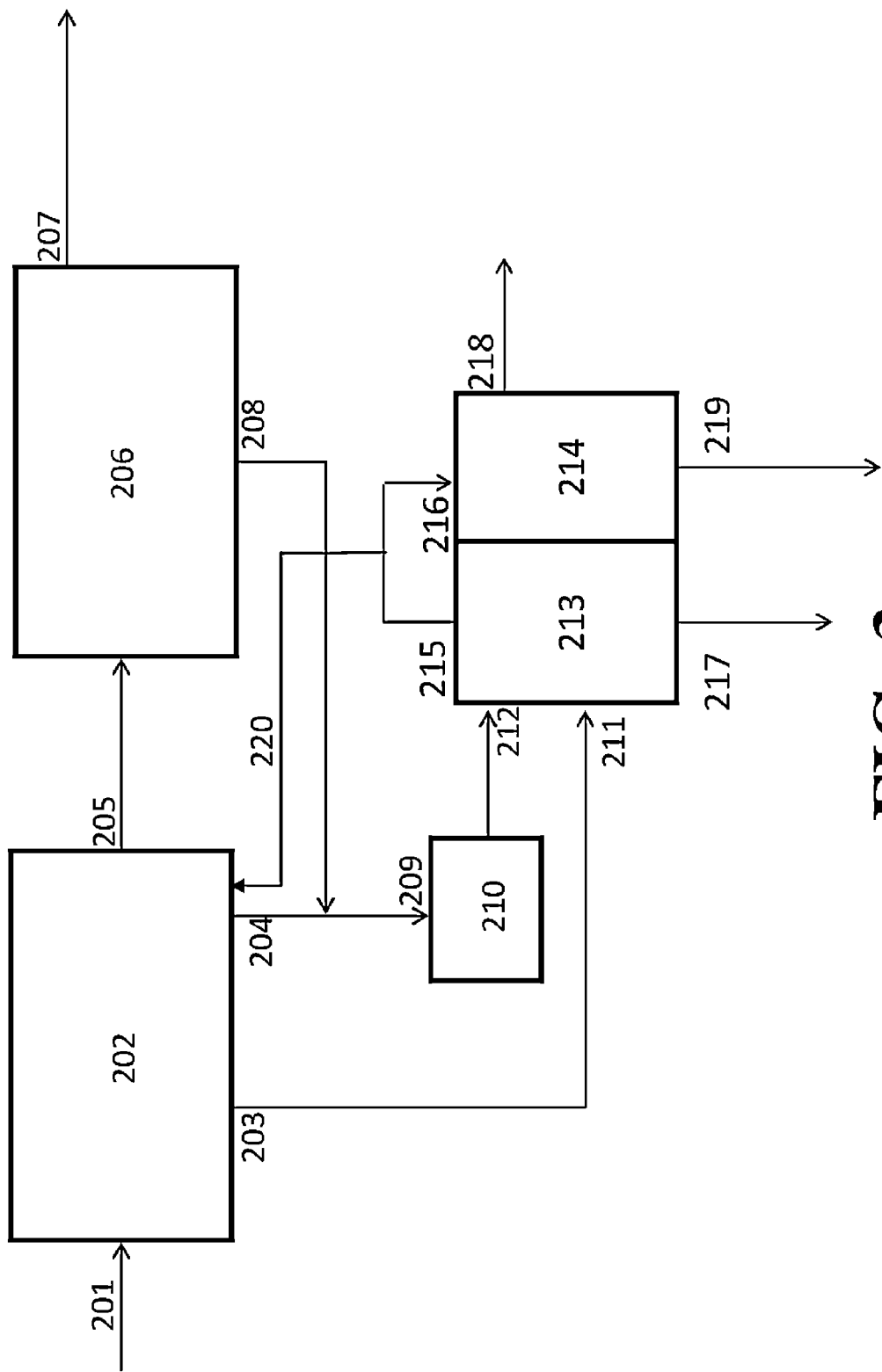
FIG. 3 represents an additional embodiment of the system for producing natural gas further including a chemical dewatering/conditioning system.

FIG. 3 depicts an additional component in one or more embodiments of the system for producing natural gas. After being digested in the anaerobic digestion system [202], the biodigestate [205] can be further treated in a physiochemical conditioning/dewatering system [206]. The chemical conditioning/dewatering system [206] is in fluid communication with the biodigestate outlet [205] of the anaerobic digestion system [202]. The physiochemical conditioning/dewatering system [206] also has a refuse outlet [207] and a centrate outlet [208]. The centrate outlet [208] may be in fluid communication with the supernatant stream coming out of the supernatant outlet [204] of the anaerobic digestion system [202]. The combined stream of centrate and supernatant may be in fluid communication with the centrate/supernatant inlet [209] of a filter [210]. The refuse produced in the physiochemical conditioning/dewatering system is removed through the refuse outlet [207] and can be further processed, disposed of, or used for other applications. Before the centrate/supernatant stream enters the RW-EDI system, it can optionally pass through a filter [210] that removes any suspended solids in the centrate/supernatant stream [209]. The filter [210] is in fluid communication with the $CO_2$ Capture portion [213] of the RW-EDI system. The RW-EDI system has, at least, a $CO_2$ Capture portion [213], a $CO_2$ Release portion [214], a cathode and an anode, not depicted. The $CO_2$ Capture portion, which can be a basic wafer, or alternatively a basic portion of the wafer, is used to capture $CO_2$ gas and convert it to bicarbonate, and release natural gas. The $CO_2$ Capture portion [213] has a biogas inlet [211], a supernatant inlet [212], a natural gas outlet [217], and a bicarbonate stream outlet [215]. The supernatant inlet [212] is in fluid communication with the filter [210], and the biogas inlet [211] is in fluid communication with the biogas outlet [203] of the anaerobic digestion system [202]. The $CO_2$ Release portion [214], which can either be an acidic wafer, or alternatively an acidic portion of the wafer, converts the bicarbonate into pure $CO_2$, resulting in the release of $CO_2$ gas through a $CO_2$ outlet [219] and a bicarbonate-depleted stream [218]. The $CO_2$ Release portion [214] has a bicarbonate inlet [216], a $CO_2$ outlet [219], and a bicarbonate-depleted stream outlet [218]. The bicarbonate inlet [216] is in fluid communication with the bicarbonate outlet [215]. Although not required, the system may also include a pathway [220] for a bicarbonate stream to be recirculated to the anaerobic digester [202] to maintain the alkalinity in the digester.

As mentioned above, the biodigestate is usually further treated through physiochemical conditioning to reduce the volume of the digestate to be disposed of. The biodigestate [205] is moved to a physiochemical conditioning/dewatering system [206] and undergoes further treatment to create a centrate stream and a refuse stream. The refuse stream includes, but is not limited to, material isolated from the treated biodigestate stream. The refuse stream [207] can either be disposed of or sent away for further processing. The centrate stream [208] may be combined with the supernatant stream from the anaerobic digestions system [204]. before entering the RW-EDI system. Before it enters the RW-EDI system, the combined centrate/supernatant stream [209] may enter a filter [210] that removes any residual solids left in the stream, becoming a filtered supernatant stream that enters the $CO_2$ Capture portion [212] of the RW-EDI system. Exemplary chemical conditioning/dewatering systems [206] may comprise a belt filter press process, a belt press process, or a centrifuge process.

In one or more embodiments, the RW-EDI system may contain a cathode, an anode, and a plurality of porous solid ion exchange resin wafers arranged in a stack that separate the cathode and anode. In one embodiment, the wafers are arranged in pairs of basic and acidic wafers having a porous basic ion exchange medium and porous acidic ion exchange medium, respectively, and with the basic wafer being in fluid communication with the acidic wafer of each pair. Alternatively, each wafer can have a basic and acidic portion, with the basic portion being in fluid communication with the acidic portion via a vented juncture. Each basic portion and acidic portion has a porous basic ion exchange medium and porous acidic ion exchange medium, respectively. Each wafer may have a thickness in range of about 1-20 mm. The thickness or other dimensions of adsorption (basic wafer) and desorption (acidic wafer) cells could be different to accommodate different rates of adsorption and desorption.

The resin wafers may be fabricated from commercial grade resins (PUROLITE® resins; The Purolite Co.). The resin wafers with different cation/anion mixing ratios may be fabricated using the process described in U.S. Pat. Nos. 6,797, 140, 7,306,934, and 7,452,920. Each basic wafer or portion contains a porous basic ion exchange medium with the fluid having a pH range between about 7-9.5. Each acidic wafer or portion contains a porous acidic ion exchange medium with the fluid having a pH range between about 5-7.

The pH of the respective wafers or portions is maintained through the application of an electric potential across the cathode and anode. The minimum voltage needed is 1V per cell pair for the desired current, although up to 12V per cell pair may be applied. The voltage per cell pair will preferably be greater than 1V if the wafer thickness is greater than 1 mm. Typically, the wafers will have a thickness in the range of about 1-20 mm, although greater wafer thickness may still work. The actual voltage will vary with the thickness of the wafer with thicker wafers requiring higher voltages. The total voltage may be calculated by the applied voltage per cell pair (A) multiplied by the total number of cell pairs (x) plus voltages of cathode and anode (E, around 3-5V). The total voltage may be represented by this expression: $Ax+E$. The determination of an appropriate working voltage is within the level of ordinary skill in the art. Preferably, the electric potential applied across the cathode and the anode is in the range of about 1-12V/cell pair.

Ion exchange membranes allow balancing counter ions to flow from one wafer to another as well as to the cathode and the anode, such that there is a net flow of protons toward the cathode and a net flow of hydroxyl ions toward the anode. This maintains a basic pH in the basic ion exchange medium, and an acidic pH in the acidic ion exchange medium.

The cathode, wafers, and anode are interleaved with bipolar ion exchange membranes, and collectively direct a net flow of protons through the wafers toward the cathode and a net flow of hydroxyl ions through the wafers toward the anode, when an electric potential is applied to across the cathode and anode. The flow of protons and hydroxyl ions, combined with the capture and release of $CO_2$ maintains a basic pH in each basic wafer or basic portion and an acidic pH in each acidic wafer or acidic portion.

The acidic ion exchange medium of the embodiments described herein may contain a carbonic anhydrase enzyme or enzyme or catalysts analogues thereto to facilitate conversion of bicarbonate ion to gaseous $CO_2$. The carbonic anhydrase enzyme can be chemically or biochemically bound to the acidic ion exchange medium, if desired. In addition, or alternatively, the basic ion exchange medium of a wafer can absorb a carbonic anhydrase enzyme or chemical catalyst to facilitate conversion of gaseous $CO_2$ to bicarbonate ion. The carbonic anhydrase enzyme can also be chemically or biochemically bound to the basic ion exchange medium, if desired.

In one embodiment, the RW-EDI apparatus comprises a cathode, an anode and at least one pair of alternating basic and acidic porous solid ion exchange resin wafers that separate the cathode and anode. A plurality of wafers is arranged in a stack, with the cathode at one end of the stack and the anode at the other end of the stack. The stack preferably comprises one or more basic wafers and a number of acidic wafers equal to the number of basic wafers. A bipolar ion exchange membrane separates the cathode and basic wafer, and a bipolar ion exchange membrane separates the anode and acidic wafer. In each pair, there is a basic wafer and an acidic wafer, with a bipolar ion exchange membrane separating each pair from the next adjacent pair. The basic and acidic wafers of each pair are in fluid communication with each other. Within each pair, a cation exchange membrane separates the basic wafer from the acidic wafer.

Figure 4:
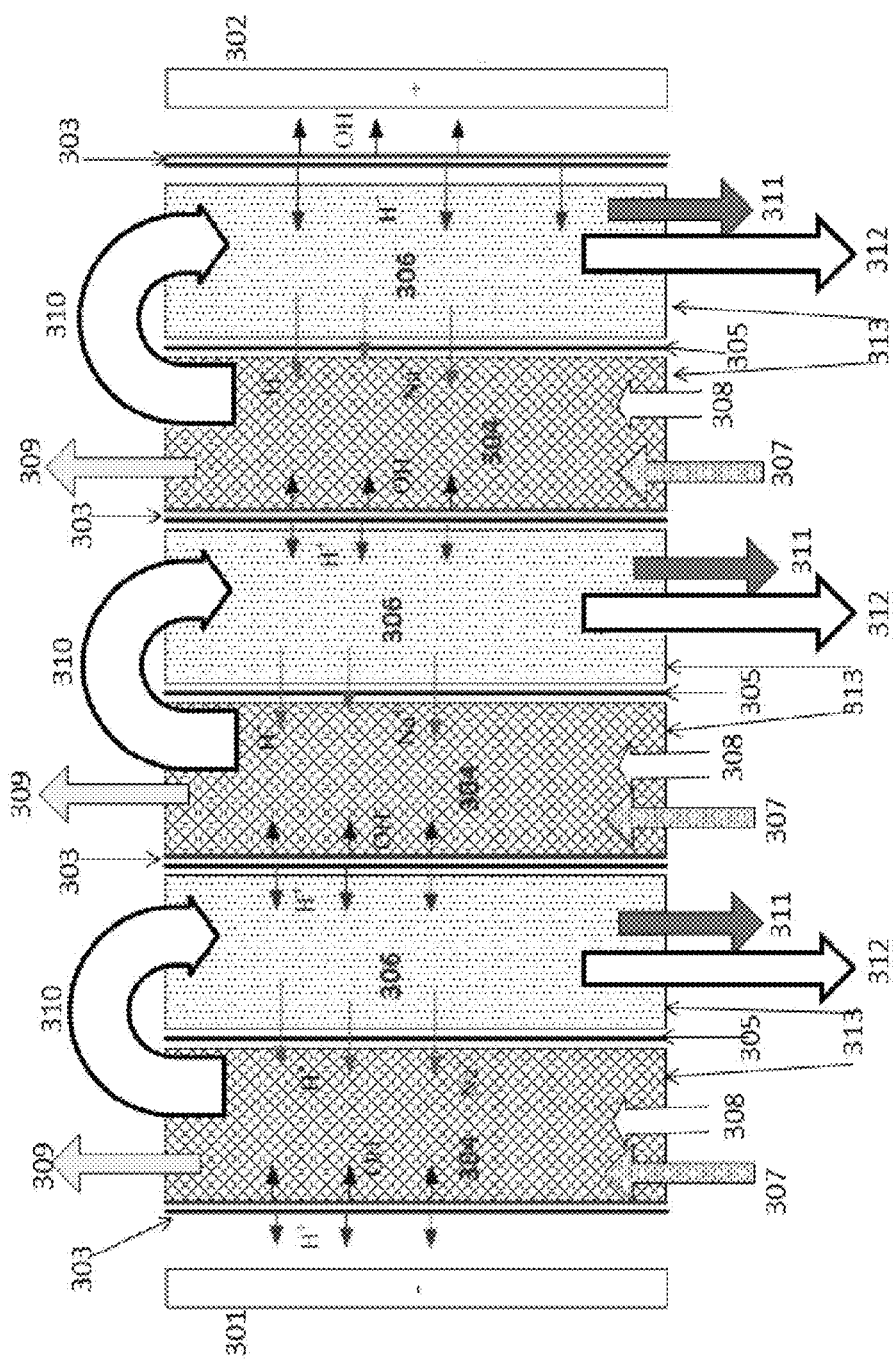
FIG. 4 represents one embodiment of the RW-EDI apparatus, in which the plurality of wafers are arranged in pairs, with one basic wafer and one acidic wafer in each pair.

FIG. 4 shows one embodiment of the RW-EDI system. It comprises a cathode [301], an anode [302], and at least one pair of wafers [313] containing a basic wafer [304] and an acidic wafer [306]. Each basic wafer [304] contains porous basic ion exchange medium, and each acidic wafer [306] contains porous acidic ion exchange medium. The cathode [301] and basic wafer [304] are separated by a bipolar ion exchange membrane [303], and the anode [302] and acidic wafer [306] are separated by a bipolar ion exchange membrane [303]. A pair of wafers [313] is separated from any adjacent pair [313] by a bipolar ion exchange membrane [303]. Within each pair of wafers [313], a cation exchange membrane [305] separates the basic wafer [304] and acidic wafer [306]. Each basic wafer [304] has a biogas inlet [307], a supernatant inlet [308], a $CO_2$-depleted, methane-enriched biogas outlet [309], and a bicarbonate outlet [310]. Each acidic wafer [306] has a bicarbonate inlet [310], a $CO_2$ outlet [311] and a bicarbonate-depleted outlet [312]. The bicarbonate outlet [310] is in fluid communication with the bicarbonate inlet [310] of the acidic wafer [306].

The pH of the respective wafers or portions is maintained through the application of an electric potential across the cathode [301] and anode [302]. The minimum voltage needed is 1V per cell pair [313] for the desired current, although up to 12V per cell pair [313] may be applied. The voltage per cell pair [313] will preferably be greater than 1V if the wafer thickness is greater than 1 mm. Typically, the wafers will have a thickness in the range of about 1-20 mm, although greater wafer thickness may still work. The actual voltage will vary with the thickness of the wafer with thicker wafers requiring higher voltages.

Each basic wafer [304] contains a porous basic ion exchange medium, and has a biogas inlet [307], a supernatant inlet [308], a natural gas outlet [309], and a bicarbonate outlet [310]. The biogas inlet [307] is in fluid communication with the biogas outlet of the anaerobic digestion system, and the supernatant inlet [308] is in fluid communication with the supernatant outlet from the anaerobic digestion system. The biogas inlet [307] and supernatant inlet [308] are each configured to introduce the biogas and supernatant to the aqueous fluid within the basic wafer to convert $CO_2$ in the biogas into bicarbonate ion and to produce a concentrated stream of natural gas.

Each acidic wafer [306] has a bicarbonate inlet [310], a $CO_2$ outlet [311], a bicarbonate-depleted stream outlet [312], and contains a porous acidic ion exchange medium. The bicarbonate outlet [310] is in fluid communication with the bicarbonate inlet [310] of the acidic wafer [306]. The acidic wafer [306] is configured to receive and convert the bicarbonate ions to $CO_2$ gas. The bicarbonate-depleted stream outlet [312] may be in fluid communication with the initial wastewater stream before it enters the wastewater treatment system. The natural gas [309] is collected, or otherwise removed, from each basic wafer [304] of the RW-EDI system. Then the bicarbonate stream [310] enters the acidic wafer [306] of the RW-EDI system, and the acidic wafer [306] facilitates conversion of bicarbonate to $CO_2$ through contact with the acidic ion exchange medium. This also results in the production of a bicarbonate-depleted stream [310]. The $CO_2$ [311] may be collected, or otherwise removed from each acidic wafer [306] of the RW-EDI system, while the bicarbonate-depleted stream [312] is removed from the acidic wafer. The various gases may be introduced or removed from the wafers or portions thereof via gas inlets and/or outlet tubes through the use of macroporous membranes or channels in contact with or connected to the wafers or portions, or by any other suitable structure.

In another embodiment, each wafer comprises a basic portion comprising a porous basic exchange medium and an acidic portion comprising a porous acidic ion exchange medium in fluid communication with the basic portion at a gas-vented juncture defined at the interface between the basic portion and the acidic portion of the wafer. Each wafer is separated from any adjacent wafer by a fluid-flow passageway in fluid communication with the basic and acidic portions of the same wafer. The passageway is defined by a spaced pair of an anion exchange membrane adjacent to one wafer and a cation exchange membrane adjacent to the next wafer in the stack in the direction from cathode to anode. The cathode is separated from an adjacent wafer by a cation exchange membrane, and the anode is separated from an adjacent wafer by a passageway defined by a spaced pair of an anion exchange membrane and a cation exchange membrane. The vented juncture between the basic and acidic portions of each wafer is adapted to collect the $CO_2$-depleted, methane-enriched biogas from the wafer. Preferably, the juncture between the basic portion and the acidic portion of each wafer comprises hollow fiber tubes adapted to collect the $CO_2$-depleted, methane-enriched biogas from the wafer. Other gas exit (gas/liquid separation) strategies known in the art are equally acceptable.

Figure 5:
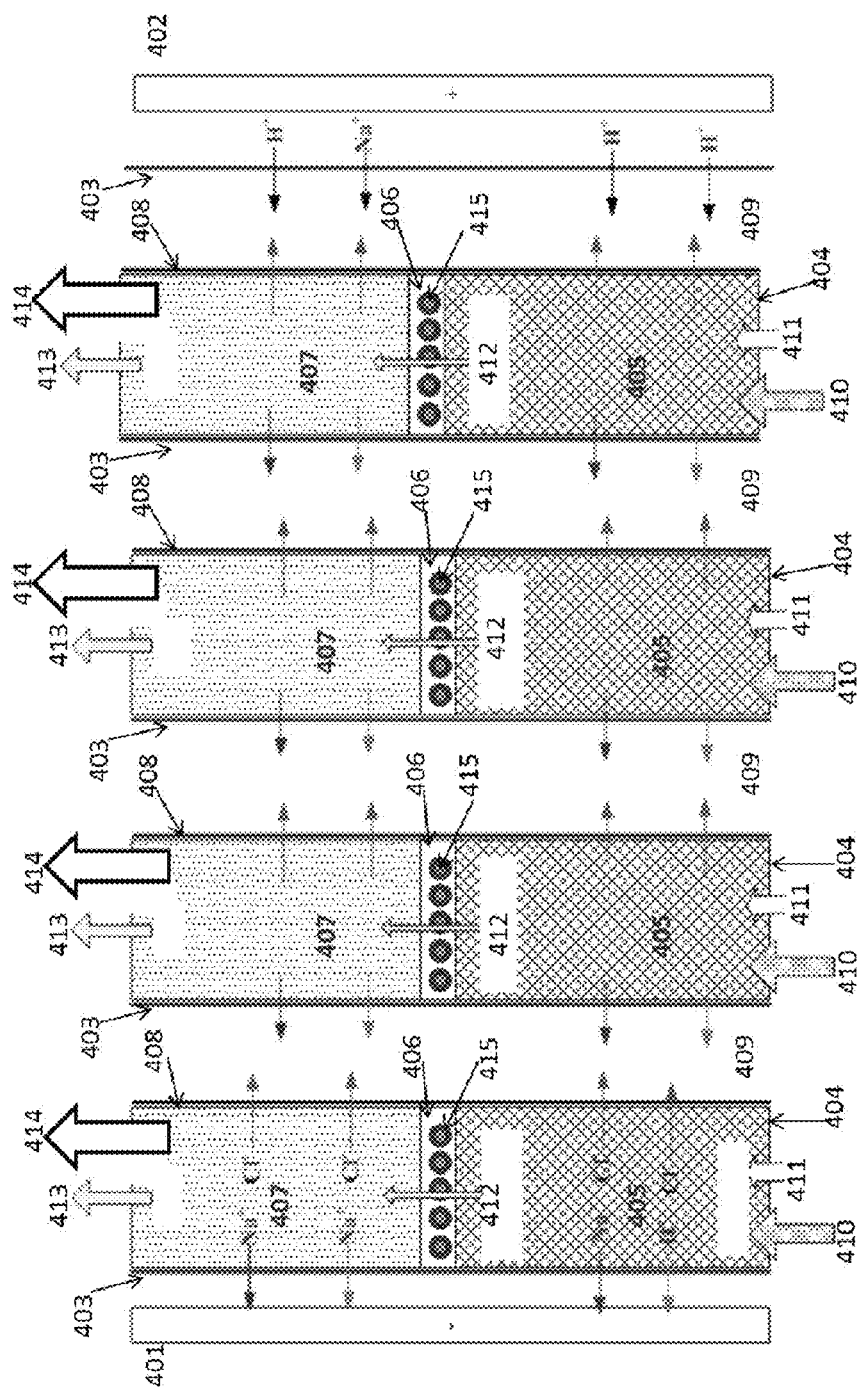
FIG. 5 represents an additional embodiment of the RW-EDI apparatus in which each wafer includes a basic portion and an acidic portion.

FIG. 5 illustrates another embodiment of the RW-EDI system. It comprises a cathode [401], an anode [402], and at least one wafer [404] separating the cathode [401] and anode [402]. A cation exchange membrane [403] separates the cathode [401] and any adjacent wafer [404], and a cation exchange membrane [403] separates the anode [402] and any adjacent wafer [404]. Each wafer [404] is separated from any adjacent wafer [404] by a fluid-flow passageway [409]. Within each wafer [404], there is a basic portion with porous basic ion exchange medium [405], and there is an acidic portion with porous acidic ion exchange medium [407]. A vented juncture [406] is inserted between the acidic [407] and basic [405] portions of the wafer [404], which can comprise of hollow tubes [416]. The hollow tubes [416] of the vented juncture [406] collect the $CO_2$-depleted, methane-enriched biogas, while the bicarbonate outlet [412] passes through the spaces between the hollow tubes [415] and enters the acidic portion [407] of the wafer [404]. Each basic portion [405] has a biogas inlet [410], a supernatant inlet [411], vented juncture for collecting $CO_2$-depleted, methane-enriched biogas [406], and a bicarbonate outlet [412]. Each acidic portion [407] has a bicarbonate inlet [412], a $CO_2$ outlet [413] and a bicarbonate-depleted stream outlet [414]. The bicarbonate outlet [412]

is in fluid communication with the bicarbonate inlet [412] of the acidic portion of the wafer [407].

During use, an electric potential is applied across the cathode [401] and anode [402] while biogas [410] flows into the basic ion exchange medium within the basic portion [405] of the wafer [404]. The basic ion exchange medium converts $CO_2$ into bicarbonate ion [412], while the natural gas is collected from each wafer through outlet junctures [406] (e.g. via hollow fiber tubes [415]). The bicarbonate outlet [412], propelled by the gas stream, flows from basic portion [405] of the wafer and into acidic portion of the wafer via juncture. The bicarbonate [412] is converted into $CO_2$ gas [413] by the acidic ion exchange medium of acidic portion [407], becoming the bicarbonate-depleted outlet [414]. The bicarbonate-depleted outlet [414] flows out of the acidic portion of the wafer [407], and can combine with the initial wastewater inlet before it enters the wastewater treatment system.

In an additional embodiment, the acidic portion of the RW-EDI apparatus is not present and, therefore, a concentrated bicarbonate solution and a concentrated natural gas stream are produced and removed from the basic portion. The concentrated bicarbonate solution could be used for enhancing algae production, or $CO_2$-related uses, or can be recycled back into the anaerobic digester to maintain alkalinity.

Figure 6:
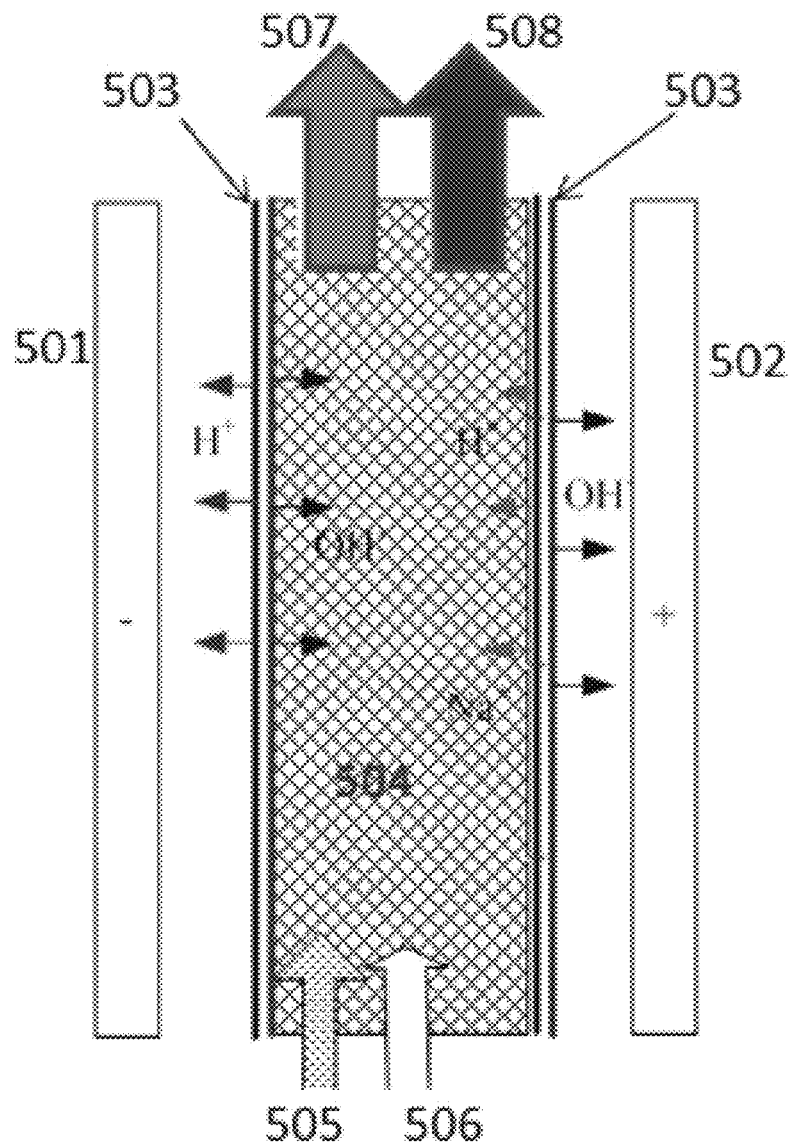
FIG. 6 represents an additional embodiment of the RW-EDI apparatus having at least one basic wafer exists in the system, but no acidic wafers.

FIG. 6 shows another embodiment, in which the acidic wafer is omitted, leaving only a basic wafer. Like the embodiment in FIG. 4, it also has a cathode [501] and an anode [502], with at least one basic wafer [504] separating the cathode [501] and the anode [502]. Each basic wafer [504] is separated from any adjacent basic wafer [504] by a bipolar ion exchange membrane [503]. A bipolar ion exchange membrane [503] separates the cathode [501] from any basic wafer [504], and a bipolar ion exchange membrane [503] separates the anode [502] from any basic wafer [504]. Each basic wafer [504] has a biogas inlet [505], a supernatant inlet [506], a natural gas outlet [507], and a bicarbonate outlet [508].

As mentioned above, the system and method described herein provide a number of benefits, including a cost-effective and energy-efficient way of anaerobically digesting organic waste and converting biogas into pure natural gas. In addition, multiple systems can be utilized to further treat the organic waste to achieve optimal yield of natural gas. Also, the RW-EDI can recycle the bicarbonates back into the digester to maintain pH and alkalinity in the digester, thereby improving performance of the digester. Furthermore, the system and method described herein can reduce greenhouse gas emissions by capturing $CO_2$ from the biogas, thereby increasing methane content in the $CO_2$-depleted, methane-enriched biogas, and sending the $CO_2$ to be used for any desired application.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A method for the production of a renewable natural gas in an integrated biodigestion and resin-wafer electrodeionization system, comprising:
   (a) anaerobically digesting a biomass to produce a biogas stream, a supernatant stream and a biodigestate stream;
   (b) introducing the biogas stream and the supernatant stream to a resin-wafer electrodeionization system (RW-EDI) to produce a $CO_2$-depleted, methane-enriched biogas, $CO_2$ and a bicarbonate-depleted stream of fluid;
   (c) removing the $CO_2$-depleted, methane-enriched biogas from the RW-EDI system;
   (d) removing the $CO_2$ gas from the RW-EDI system.

2. The method of claim 1, further comprising the steps of:
   (a) providing an initial wastewater stream containing biomass;
   (b) treating the initial wastewater stream to produce treated wastewater and biomass;
   (c) removing the treated wastewater.

3. The method of claim 2, wherein producing a $CO_2$-depleted, methane-enriched biogas, $CO_2$ and a bicarbonate-depleted stream of fluid comprises:
   (a) introducing the biogas stream and supernatant to an aqueous fluid within the basic ion exchange medium of a basic portion of a wafer of the RW-EDI system;
   (b) applying an electric potential across the cathode and anode of the RW-EDI system;
   (c) removing the $CO_2$-depleted, methane-enriched biogas stream from the RW-EDI system;
   (d) introducing bicarbonate stream into an aqueous fluid within the acidic ion exchange medium of an acidic portion of the RW-EDI system to produce $CO_2$ and a bicarbonate-depleted stream;
   (e) removing the $CO_2$ gas from the RW-EDI system;
   (f) recirculating the bicarbonate-depleted stream into initial wastewater stream.

4. The method of claim 3, wherein removing the $CO_2$-depleted, methane-enriched biogas and $CO_2$ from the RW-EDI system comprises:
   (a) collecting the $CO_2$-depleted, methane-enriched biogas from a vented juncture of each wafer of the RW-EDI system; and (b) collecting the $CO_2$ gas from each acidic portion of the wafer of the RW-EDI system.

5. The method of claim 4, wherein the electric potential applied across the cathode and anode is at least about 1 volt per cell pair.

6. The method of claim 4, wherein the pH of the aqueous fluid within the basic ion exchange medium of each wafer is maintained in the range of about 7 to about 9.5 by application of the electric potential across the cathode and anode, and the pH of the aqueous fluid within the acidic ion exchange medium of each wafer is maintained in the range of about 5 to 7 by application of the electric potential across the cathode and anode.

7. The method of claim 1, wherein the biomass is selected from the groups consisting of: sludge from wastewater treatment plants; animal manure; plant, agricultural, and lignocellulosic materials; algal biomass; municipal solid waste; forest, wood and paper residues; coal; organic solid waste; pet coke; hydrocarbon residues; food wastes; and combinations thereof.

8. The method of claim 1, further comprising the step of thickening the biomass prior to anaerobically digesting the biomass.

9. The method of claim 1, further comprising the step of treating the biodigestate produced during the step of anaerobically digesting the biomass.

10. The method of claim 1, further comprising the step of adding alkaline silicate minerals to the step of anaerobically digesting a biomass, wherein at least a portion of $CO_2$ produced during anaerobic digestion is sequestered as insoluble alkaline carbonates.

11. The method of claim 1, wherein producing a $CO_2$-depleted, methane-enriched biogas, $CO_2$ and a bicarbonate-depleted stream of fluid comprises:
   (a) providing a biogas stream and supernatant to a RW-EDI system into an aqueous fluid within a basic wafer to produce a $CO_2$-depleted, methane-enriched biogas stream and a bicarbonate stream;
   (b) applying an electric potential across a cathode and anode of the RW-EDI system;
   (c) removing the $CO_2$-depleted, methane-enriched biogas from the RW-EDI system;
   (d) introducing the bicarbonate stream to an acidic wafer in the RW-EDI system to produce $CO_2$ and a bicarbonate-depleted stream;
   (e) removing the $CO_2$ from the RW-EDI system; and
   (f) recirculating the bicarbonate-depleted stream into the initial wastewater stream.

12. The method of claim 11, further comprising the step of: recycling a portion of the bicarbonate stream from the basic wafer to the anaerobic digester to maintain the alkalinity in the digester.

13. The method of claim 11, wherein removing the $CO_2$-depleted, methane-enriched biogas and $CO_2$ from the RW-EDI system comprises:
   (a) collecting the $CO_2$-depleted, methane-enriched biogas from each basic wafer; and
   (b) collecting the $CO_2$ gas from each acidic wafer.

14. The method of claim 13, wherein the electric potential applied across the cathode and anode is at least about 1 volt per cell pair.

15. The method of claim 13, wherein the pH of the aqueous fluid within each basic wafer is maintained in the range of about 7 to about 9.5 by application of the electric potential across the cathode and anode, and the pH of the aqueous fluid within each acidic wafer is maintained in the range of about 5 to 7 by application of the electric potential across the cathode and anode.

16. A system for generating $CO_2$-depleted, methane-enriched biogas comprising:
   an anaerobic digestion apparatus comprising a biomass inlet, a biogas outlet, a supernatant outlet, and a biodigestate outlet; and
   a resin-wafer electrodeionization (RW-EDI) apparatus comprising a biogas inlet, a supernatant inlet, a $CO_2$-depleted, methane-enriched biogas outlet, and a $CO_2$ outlet;
   wherein the biogas outlet and the supernatant outlet are in fluid communication with the RW-EDI system.

17. The system of claim 16, further comprising a wastewater treatment apparatus comprising a wastewater inlet, a treated water outlet and a biomass outlet, wherein the biomass outlet is in fluid communication with the biomass inlet of the anaerobic digestion apparatus.

18. The system of claim 16, wherein the RW-EDI apparatus further comprises a bicarbonate-depleted stream outlet, wherein the bicarbonate-depleted stream outlet is in fluid communication with the wastewater inlet.

19. The system of claim 16, further comprising a physiochemical conditioning/dewatering apparatus, wherein the physiochemical conditioning/dewatering system comprises a biodigestate inlet, a refuse outlet, and a centrate outlet, and wherein the biodigestate outlet of the anaerobic digestion apparatus and the biodigestate inlet are in fluid communication with each other.

20. The system of claim 19, wherein the supernatant stream outlet combines with the centrate outlet before entering the resin-wafer deionization apparatus.

21. The system of claim 16, wherein the RW-EDI apparatus comprises a cathode, an anode, and at least one pair of an alternating basic porous solid ion exchange resin wafer and an acidic porous solid ion exchange resin wafer with a basic and acidic wafer in each pair;
   wherein the cathode and the anode are separated by one or more pairs of wafers arranged in stack;
   wherein each pair of wafers is separated from any adjacent pair by a bipolar ion exchange membrane;
   wherein a cation exchange membrane is between the basic wafer and the acidic wafer of each pair;
   wherein a bipolar ion exchange membrane is between the cathode and a basic wafer, and a bipolar ion exchange membrane is between the anode and an acidic wafer;
   wherein each basic wafer comprises a porous basic ion exchange medium and each acidic wafer comprises a porous acidic ion exchange medium;
   wherein each basic wafer further comprising a biogas inlet, a supernatant inlet, a natural gas outlet, and a bicarbonate outlet,
   wherein each acidic wafer comprises a bicarbonate inlet, a carbon dioxide outlet, and a bicarbonate-depleted stream outlet.

22. The system of claim 16, wherein the RW-EDI apparatus comprises a cathode, an anode, and at least one porous solid ion exchange resin wafer;
   wherein the cathode and the anode are separated by a plurality of porous solid ion exchange resin wafers arranged in stack;
   wherein each wafer comprises a basic portion containing a porous basic ion exchange medium and an acidic portion containing a porous acidic ion exchange medium, and each wafer is separated from any adjacent wafer by a fluid-flow passageway in fluid communication with the basic and acidic portions of the same wafer;

wherein the cathode is separated from any adjacent wafer by a cation exchange membrane, and an anode is separated from any adjacent wafer by a fluid-flow passageway that is defined by a spaced pair of an anion exchange membrane and a cation exchange membrane;

wherein the basic ion exchange medium is in fluid communication with the acidic ion exchange medium of the same wafer at a gas-vented juncture defined at an interface between the basic portion of the wafer and the acidic portion of the wafer.

23. The system of claim 22, wherein the basic portion of the wafer comprises a biogas inlet, a supernatant stream inlet, a natural gas outlet, and a bicarbonate stream outlet;

wherein the acidic portion of the wafer comprises a bicarbonate stream inlet, a $CO_2$ gas outlet, and a bicarbonate-depleted stream outlet.

24. The system of claim 16, wherein the anaerobic digestion apparatus comprises an acid phase digester, and a gas phase digester;

wherein the acid phase digester is configured to convert organic matter into soluble compounds and fatty acids;

wherein the gas phase digester is configured to convert the soluble matter into biogas.

25. A system for generating natural gas, the system comprising:

a wastewater treatment apparatus comprising a wastewater inlet, a treated water outlet, and a biomass outlet;

an anaerobic digestion apparatus comprising a biomass inlet, a biogas outlet, a supernatant outlet, and a biodigestate outlet; and a resin-wafer electrodeionization (RW-EDI) apparatus comprising a biogas inlet, a supernatant inlet, a natural gas outlet, a bicarbonate outlet, wherein the biomass outlet is in fluid communication with the biomass inlet, and wherein the biogas outlet and the centrate outlet are in fluid communication with the RW-EDI system, wherein the RW-EDI apparatus comprises a cathode, an anode, and at least one basic porous solid ion exchange resin wafer;

wherein the cathode and anode are separated by a plurality of porous solid ion exchange resin wafer arranged in a stack between the cathode and the anode;

wherein the cathode, the anode, and the wafers are interspersed with ion exchange membranes;

wherein each basic wafer comprises a porous basic ion exchange medium;

wherein the basic wafer comprises a biogas inlet, a supernatant stream inlet, a natural gas outlet, and a bicarbonate stream outlet; and wherein the bicarbonate stream outlet is in fluid communication with the initial wastewater stream inlet.

\* \* \* \* \*